(12) United States Patent
Plojoux et al.

(10) Patent No.: US 9,854,845 B2
(45) Date of Patent: Jan. 2, 2018

(54) ELONGATE AEROSOL-GENERATING DEVICE AND SYSTEM

(71) Applicant: Philip Morris Products S.A., Neuchatel (CH)

(72) Inventors: Julien Plojoux, Geneva (CH); Dani Ruscio, Cressier (CH); Laurent Manca, Sullens (CH)

(73) Assignee: Philip Morris Products S.A., Neuchatel (CH)

( * ) Notice: Subject to any disclaimer, the term of this patent is extended or adjusted under 35 U.S.C. 154(b) by 488 days.

(21) Appl. No.: 14/370,355

(22) PCT Filed: Dec. 28, 2012

(86) PCT No.: PCT/EP2012/077089
§ 371 (c)(1),
(2) Date: Jul. 2, 2014

(87) PCT Pub. No.: WO2013/102614
PCT Pub. Date: Jul. 11, 2013

(65) Prior Publication Data
US 2014/0366900 A1    Dec. 18, 2014

(30) Foreign Application Priority Data

Jan. 3, 2012 (EP) ..................................... 12150114
Feb. 13, 2012 (EP) ..................................... 12155245

(51) Int. Cl.
*A24F 47/00* (2006.01)
*A61M 15/06* (2006.01)
*A61M 11/04* (2006.01)

(52) U.S. Cl.
CPC ......... *A24F 47/008* (2013.01); *A61M 11/042* (2014.02); *A61M 15/06* (2013.01); *A61M 11/047* (2014.02); *A61M 2205/8206* (2013.01)

(58) Field of Classification Search
None
See application file for complete search history.

(56) References Cited

U.S. PATENT DOCUMENTS

| 1,674,617 A | 6/1928 | De Benedictis |
| 4,327,748 A * | 5/1982 | Divis ..................... A24F 13/02 |
| | | 131/187 |

(Continued)

FOREIGN PATENT DOCUMENTS

| CN | 101862038 | 10/2010 |
| CN | WO 2011127644 A1 * | 10/2011 ........... A24F 47/008 |

(Continued)

OTHER PUBLICATIONS

International Search Report dated Oct. 4, 2013 in PCT/EP12/077089 Filed Dec. 28, 2012.

(Continued)

*Primary Examiner* — Eric Yaary
(74) *Attorney, Agent, or Firm* — Oblon, McClelland, Maier & Neustadt, L.L.P.

(57) ABSTRACT

There is provided an elongate aerosol-generating device having at least a portion of its transverse external cross-section defined by a shape having at least five sides. The shape may be polygonal. The cross-sectional shape of the device confers stability against rolling. The elongate aerosol-generating device includes a substrate receiving cavity configured to receive an aerosol-forming substrate to form an aerosol, a heating element, and a power supply configured to provide power to the heating element. The external shape of the aerosol-generating device may be defined by a housing having at least two separable portions. The external shape may be defined by a polygon having convexly curved faces to minimize perceived misalignments between adjacent housing portions.

10 Claims, 8 Drawing Sheets

(56) References Cited

U.S. PATENT DOCUMENTS

| | | | | |
|---|---|---|---|---|
| 6,014,009 | A * | 1/2000 | Wierzbicki | H01M 2/1022 320/106 |
| 2006/0196518 | A1 | 9/2006 | Hon | |
| 2008/0021072 | A1* | 1/2008 | Luzenberg | A24F 47/002 514/343 |
| 2008/0092912 | A1* | 4/2008 | Robinson | A24F 47/008 131/200 |
| 2010/0031968 | A1* | 2/2010 | Sheikh | A24F 47/008 131/347 |
| 2010/0307518 | A1* | 12/2010 | Wang | A24F 47/008 131/329 |
| 2010/0313901 | A1 | 12/2010 | Fernando et al. | |
| 2013/0019887 | A1* | 1/2013 | Liu | A24F 47/008 131/329 |

FOREIGN PATENT DOCUMENTS

| | | |
|---|---|---|
| EA | 012169 B1 | 8/2009 |
| EA | 012481 B1 | 10/2009 |
| FR | 2 354 720 | 1/1978 |
| GB | 741 101 | 11/1955 |
| GB | 2 301 040 A | 11/1996 |
| JP | 2006-524494 A | 11/2006 |
| KR | 10-2011-0079587 A | 7/2011 |
| RU | 110 608 U1 | 8/2011 |
| TW | 318780 | 11/1997 |
| WO | WO 2006/082571 A1 | 8/2006 |
| WO | WO 2008/013733 A2 | 1/2008 |
| WO | WO 2010/133342 A1 | 11/2010 |

OTHER PUBLICATIONS

International Preliminary Report on Patentability and Written Opinion dated Jul. 8, 2014 in PCT/EP2012/077089.
Extended European Search Report dated Oct. 26, 2012 in Patent Application No. 12150114.2.
Office Action dated Apr. 7, 2016 in Korean Patent Application No. 10-2014-7019078 (with English language translation).
Australian Notice of Acceptance dated Oct. 25, 2016 in corresponding Australian Application No. 2012364365, citing documents AO and AP therein (2 pages).
English Translation of the Decision to Grant issued Mar. 30, 2017 for Russian Application No. 2014132076 (4 pages), citing documents AO through AR therein.
English translation of Office Action dated Jun. 29, 2017 in counterpart Taiwanese Patent Application No. 101150957, citing document AO therein.

* cited by examiner

ELONGATE AEROSOL-GENERATING DEVICE AND SYSTEM

CROSS REFERENCE TO RELATED APPLICATION

This application is a national phase application based on PCT/EP2012/077089, filed on Dec. 28, 2012.

The specification relates to an aerosol-generating device with an external cross-section defined by a shape having at least 5 sides. The specification also relates to a system comprising the aerosol-generating device and a charging device for receiving the aerosol-generating device.

Aerosol-generating articles in which an aerosol-forming substrate, such as a tobacco containing substrate, is heated rather than combusted are known in the art. The aim of such heated aerosol-generating articles is to reduce known harmful smoke constituents produced by the combustion and pyrolytic degradation of tobacco in conventional cigarettes. Typically in such heated aerosol-generating articles, an inhalable aerosol is generated by the transfer of heat from a heat source to a physically separate aerosol-forming substrate or material, which may be located within, around or downstream of the heat source. During consumption, volatile compounds are released from the aerosol-forming substrate by heat transfer from the heat source and entrained in air drawn through the aerosol-generating article. As the released compounds cool, they condense to form an aerosol that is inhaled by the consumer.

A number of prior art documents disclose aerosol-generating devices for consuming heated aerosol-generating articles. Such devices include, for example, heated smoking systems and electrically heated smoking systems and smoking articles containing a tobacco-based aerosol-forming substrate consumed using such systems.

It would be desirable to provide such an aerosol-generating device that is ergonomic to hold in use. It would also be desirable to provide such a device that remains stationary while not in use, for example, an aerosol-generating device that resists rolling when set down on a flat surface.

It is also known in the art to provide a secondary device for charging the aerosol-generating device while the aerosol-generating device is not in use, referred to as a charging device or secondary device herein. Providing such a charging device allows the aerosol-generating device to be smaller and lighter. The charging device may also provide means for storing information relating to the usage of the aerosol-generating device that is downloaded from the aerosol-generating device when coupled with the charging device. If the connections between the connections of an aerosol-generating device are incorrectly coupled to contacts of a secondary device, such as a charging device, damage may be done to electronics within one or both devices.

It would be desirable to provide an aerosol-generating system comprising an aerosol-generating device and a secondary device for charging the aerosol-generating device that reduces the possibility of incorrectly connecting the aerosol-generating device to the secondary device.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may comprise one or more components used to supply energy from a power supply to an aerosol-forming substrate to generate an aerosol. For example, an aerosol-generating device may be a heated aerosol-generating device. An aerosol-generating device may be an electrically heated aerosol-generating device or a gas-heated aerosol-generating device. An aerosol-generating device may be a smoking device that interacts with an aerosol-forming substrate of an aerosol-generating article to generate an aerosol that is directly inhalable into a user's lungs thorough the user's mouth.

As used herein, the term 'aerosol-forming substrate' relates to a substrate capable of releasing volatile compounds that can form an aerosol. Such volatile compounds may be released by heating the aerosol-forming substrate. As an alternative to heating or combustion, in some cases volatile compounds may be released by a chemical reaction or by a mechanical stimulus, such as ultrasound. An aerosol-forming substrate may be solid or liquid or comprise both solid and liquid components. An aerosol-forming substrate may be adsorbed, coated, impregnated or otherwise loaded onto a carrier or support. An aerosol-forming substrate may conveniently be part of an aerosol-generating article or smoking article.

An aerosol-forming substrate may comprise nicotine. An aerosol-forming substrate may comprise tobacco, for example may comprise a tobacco-containing material containing volatile tobacco flavour compounds, which are released from the aerosol-forming substrate upon heating. In preferred embodiments an aerosol-forming substrate may comprise homogenised tobacco material, for example cast leaf tobacco. An aerosol-forming substrate may comprise at least one aerosol-former, such as propylene glycol or glycerine.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. The term 'aerosol-generating article' is generally used hereafter.

Preferably an aerosol-generating article is a heated aerosol-generating article, which is an aerosol-generating article comprising an aerosol-forming substrate that is intended to be heated rather than combusted in order to release volatile compounds that can form an aerosol. The aerosol formed by heating the aerosol-forming substrate may contain fewer known harmful constituents than would be produced by combustion or pyrolytic degradation of the aerosol-forming substrate. An aerosol-generating article may be, or may comprise, a tobacco stick.

In one aspect there is provided an elongate aerosol-generating device in which at least a portion of the device has a transverse external cross-section defined by a shape having at least five sides. It is preferred that the aerosol-generating device has a high aspect ratio and that a substantial proportion of the length has the defined cross-section. The entire length of the device may have the defined transverse cross-section.

The external cross-section may be a polygonal transverse cross-section. The polygon comprises at least five sides. The polygon may comprise at least six sides.

The device may be greater than 60 mm in length. The device may be less than 150 mm in length. For example, the device may be between 80 mm and 120 mm in length. The device may be between 90 mm and 110 mm in length.

An outer circumcircle of the transverse cross-sectional shape may have a diameter of greater than 10 mm. An outer circumcircle of the transverse cross-sectional shape may have a diameter of less than 20 mm. An outer circumcircle of the transverse cross-sectional shape may have a diameter of between 12 mm and 16 mm. The cross-section of a polygon may be defined by line passing from one edge of the polygon, through the centre of the polygon, and to an opposing edge. The length of this line may be between 10 mm and 20 mm, preferably between 12 mm and 15 mm. An even sided polygon may have a cross-sectional line that passes from a flat face of the polygon to an opposing flat face of the polygon. This distance may be, for example between 12 mm and 14 mm. An even sided polygon may have a cross-sectional line that passes from a corner of the polygon to an opposing corner of the polygon. This distance may be, for example between 12 mm and 14 mm. The corner to corner cross-section will be slightly longer than the face to face cross-section.

The sides of the cross-sectional shape may all have equal length. The sides of the cross-sectional shape may have differing lengths. Preferably one or more sides have a length greater than 2 mm, preferably greater than 3 mm or greater than 4 mm. It may be advantageous for one or more sides to have a length greater than 5 mm. The length of a side of the cross-sectional shape may be the same as a width of a facet of the three-dimensional device. For example, if the device is substantially cylindrical and has a cross-section that is an equilateral hexagon with sides of length 5 mm, the device will have six longitudinal facets of 5 mm width.

The transverse cross-sectional shape preferably has at least five corners joined by either straight lines or curves to form the shape having at least five sides. Where the corners are joined by curves it is preferable that the curves have a large radius compared to the length of the side so that the side only slightly deviates from linear and gives the appearance of being almost flat.

The aerosol-generating device may be substantially cylindrical. The term cylindrical as used herein describes a three-dimensional shape that has substantially parallel sides and a base defined by a two-dimensional shape. The two-dimensional shape is that defined for the transverse cross-section, i.e., a shape having at least five sides. The term cylinder as used herein may be equivalent to the term prismatic. By substantially parallel it is meant that the sides do not need to be precisely parallel. For example, the sides may be within plus or minus 5 degrees from true parallel.

A portion of the aerosol-generating device may be shaped as an elongate frusto-pyramid having converging sides and a base defined by a two-dimensional shape. The two-dimensional shape is that defined for the transverse cross-section, i.e., a shape having at least 5 sides.

Preferably, each of the sides of the 2-dimensional shape defining the cross-section corresponds to an elongated face on an external surface of the device.

By providing an aerosol-generating device with such a multi-faceted cross-sectional shape the surface area of the device is increased as compared to a device having a circular cross-section. For example, a device that is substantially cylindrical and having a transverse cross-section in the shape of a polygon with at least 5 sides advantageously provides a user with a more ergonomic feel, while increasing the stability of the device when it is placed on a surface while it is not in use. It is anticipated that a user may wish to place the device on a flat surface, for example a table. If the device were to roll, the user may be inconvenienced. A device comprising shape features that help stabilise the device and resist rolling will be advantageous.

The cross-sectional shape, for example a polygon, may comprise between 6 and 16 sides, preferably between 7 and 12 sides. In one preferred embodiment the shape is a polygon comprising 10 sides.

The polygon may be a regular polygon. The term regular polygon refers to a polygon that is equiangular, all of the angles are the same, and equilateral, all of the sides are the same length. The sides may be straight or slightly curved. The angles may be formed by sharp corners or rounded corners. The aerosol-generating device may have a regular polygonal transverse cross-section along its entire length. Alternatively, the aerosol-generating device may have a regular polygonal cross-section that extends along only a portion of its length. For example, the cross-section of the aerosol-generating device may change due to the presence of a button. Such a button may be adapted to activate the device in use. The position of the button may be chosen so as to facilitate presentation of the button on an uppermost surface regardless of the shape of the device.

As used herein, the term "length" refers to the dimension in the longitudinal direction. The term "longitudinal" refers to the main axis of the elongate aerosol-generating device. As used herein, the term "transverse" refers to a direction perpendicular to the longitudinal direction.

At least one end of the aerosol-generating device may be tapered. Alternatively, both ends of the aerosol-generating device may be tapered. Preferably, the radius of the or each end face of the tapered end is at least 50% of the maximum radius of the aerosol-generating device. The radius of a polygon is measured from the centroid of the polygon to a vertex thereof.

Where the at least one end of the aerosol-generating device is tapered, preferably, the at least one end of the aerosol-generating device is tapered along at least about 5% of the length of the device. More preferably, the at least one end of the aerosol-generating device is tapered along at least about 7% of the length of the device. Yet more preferably, the at least one end of the aerosol-generating device is tapered along at least about 7.5%.

Where the at least one end of the aerosol-generating device is tapered, the taper may be linear or curved. The presence of a taper may be particularly advantageous where one end of the device is configured to be inserted into and couple with another device. For example, one or more electrical contacts may be located at or near a first end of the device such that they can be brought into contact with electrical contacts located within a receiving cavity of another device. A tapered end of the device, in conjunction with a mating receiving portion, allows the device to be coupled swiftly and easily by a user. The taper guides the device into a correct position within the receiving cavity. Due to the guiding effect provided by the taper, it is possible for a user to couple the device to another device, for example a charging unit, without looking at the device to align the contacts. This may be advantageous as the act of coupling the device to another device can be carried out in the dark or while a user is engaged in conversation.

The user of an aerosol-generating device may wish to rest the device on a surface when consuming an aerosol-generating article. It may be undesirable to lay the device down as a mouth end of the article may then come into close proximity to the surface, which may be unhygienic. It may be preferable to lean the device such that the mouth end of the article is raised from the surface. Advantageously, the presence of a taper may facilitate the leaning of the device in contact with both the surface and a stationary object raised above the surface. The taper, in conjunction with a shaped cross-section, causes a large surface area to be in contact with the surface when the device is leant at an appropriate angle. This may increase the stability of the device when it is leant at an angle. The optimum leaning angle may depend on the angle of the taper. An optimum leaning angle may, for example, be between 25 degrees and 60 degrees from the surface.

Preferably, the elongate aerosol-generating device comprises an outer housing having a substrate receiving cavity adapted to receive an aerosol-generating article including an aerosol-forming substrate, a heating element adapted to heat an aerosol-forming substrate to generate an aerosol, and a power supply adapted to provide power to the heating element. The device may also comprise a controller for controlling the power supplied from the power supply to the heating element.

Where the aerosol-generating device comprises a substrate receiving cavity, a holder may be provided within the cavity. The holder is adapted to hold an aerosol-forming substrate adjacent the end of the aerosol-generating device having the cavity. The aerosol-forming substrate is itself preferably a component part of an aerosol-generating article that is receivable in the holder.

The external shape of the device may be defined by a housing. The housing may form a shell retaining component parts of the device. The housing may have an internal cross-section that is the same shape as its external cross-section. The housing may have an internal cross-section that is circular. The housing may have an internal cross-section that is non-circular and of different shape to the external cross-section.

Where the device comprises a holder adapted to hold an aerosol-generating article including an aerosol-forming substrate, a plurality of air inlets leading to a plurality of air channels within the device may be formed by a space between the holder and the outer housing portion. For example, the holder may have a circular external cross-section and the housing may have a decagonal internal cross-section. If the holder is fitted within the housing such that an outer portion of the holder contacts each of the ten inner faces of the internal surface of the housing, ten gaps are defined by spaces between corners of the decagon and the holder. These gaps may act as air inlets. The area of air inlets may be controlled by selecting the internal shape of the housing, or selecting the internal shape of the housing in the portion of housing defining the substrate receiving cavity.

The air channels may diverge away from the air inlets within the device as the outer housing diverges with tapering. Providing such air channels may improve the air entrainment within the device. In addition, the entrained air may improve the insulation between the aerosol-forming substrate and the outer housing.

The substrate receiving cavity may be adapted to receive an aerosol-generating article having a mouth end and a distal end, an aerosol-forming substrate being located at the distal end. The distal end of the aerosol-generating article is inserted into the substrate receiving cavity.

In use, a user inserts an aerosol-generating article into the substrate receiving cavity of the device, activates the device, applies his or her lips to the mouth end of the aerosol-generating article, and inhales. Air and any aerosol generated within the device are drawn through the mouth end of the aerosol-generating article to be inhaled by the user. When the user inhales, air and aerosol move through the aerosol-generating article from the distal end to the mouth end. In some embodiments, air may be drawn into the device through the end of the device proximal to the aerosol-generating article. In some embodiments, air may be drawn into the device through a sidewall. In other embodiments, air may be drawn into the device through a combination of the proximal end of the device and a sidewall of the device.

The aerosol-generating article may be substantially cylindrical in shape. The aerosol-generating article may be substantially elongate. The aerosol-generating article may also have a length and a circumference substantially perpendicular to the length. The aerosol-generating article may be received in the cavity of the aerosol-generating device such that the length of the aerosol-generating article is substantially parallel to the airflow direction in the aerosol-generating device.

Where the aerosol-generating device has a housing, the housing may be an elongate shell having a length of between 60 mm and 150 mm. The housing may have a wall thickness of between 0.2 mm and 1 mm. If the housing is formed from a metallic material the wall thickness is preferably between 0.2 mm and 0.4 mm. If the housing is formed from a polymer the wall thickness is preferably between 0.5 mm and 1 mm, for example between 0.6 mm and 0.8 mm, or about 0.75 mm.

The outer housing of the aerosol-generating device may be manufactured from two, four or more portions. The portions are preferably joined together along a transverse cross-section of the device, and may be adapted to join around one or more buttons protruding from the device. Where the outer housing comprises four portions, the portions may be two tapered end portions, and two substantially cylindrical central portions. In some embodiments a first housing portion may define the external shape of a first end of the device and a second housing portion may define the external shape of a second end of the device. Two adjacent housing portions may meet at a join situated approximately half-way along the length of the device. Two housing portions may meet at a join that lies closer to one end of the device than the other. Preferably the housing portions are separable, for example a first housing portion may be capable of being separated from a second housing portion by sliding the housing portions apart in a longitudinal direction. Access to an internal portion of the device may be obtained by removing one or more portions of housing.

It may be preferable that the aerosol-generating device comprises a housing portion that is fixed to internal components of the device, and cannot be removed from the device, and a further housing portion that can be removed from the device. It may be preferable that an end of the device that comprises the substrate receiving cavity may be removable from the device. Any holder within the substrate receiving cavity may be removed with the housing portion. Removal of a portion of the housing may be desirable in order to access inner component parts of the device, for example to clean the device. Movement of a housing portion, or removal of a housing portion may also be desirable in order to assist removal of aerosol-generating articles after use of the device.

Where a housing portion is removable from the device it may be desirable that the housing portion should only be couplable to the device in a specific orientation. The removable housing portion may, for example, slide over a substantially cylindrical inner portion of the device. In such circumstances an inner surface of the housing may define a notch or a protrusion that keys with a corresponding protrusion or notch on the inner portion to ensure that the housing portion may only be coupled to the aerosol-generating device in a specific orientation.

Where a housing portion is slideable with respect to inner components of the device, it may be advantageous if the housing portion can be retained in one or more stable positions. To this effect the inner surface of the housing portion may comprise protrusions that engage with a protrusion defined on an inner portion of the device to act as snaps. For example, two longitudinally spaced protrusions on the inner surface of the may engage with a protrusion on the inner portion of the device to locate the housing portion. Preferably the protrusion on the inner portion is sprung such that it can be made to pass the protrusions on the housing on the application of a force. It may be particularly advantageous that the inner surface of the housing has a non-circular cross-sectional shape, for example a polygonal shape. By locating protrusions at corners of the inner surface of the housing it is possible to control the properties of the snaps to optimise their function. A removable housing portion may have a set of snaps that hold the housing portion in a fully closed position adjacent a second housing portion. There may be a second set of snaps that retain the housing portion in a second position that is slideably removed from the first position, but still attached to the device. The relative strength of different sets of snaps may be varied.

Where an external housing comprises two or more separate portions, the visual appearance of the device may be impaired if the two or more portions do not align with precision. For example, if the device is in the form of a cylinder having a polygonal base, any mismatch or misalignment between adjacent housing portions will become immediately apparent when the housing portions are brought together. This may be a result of light reflecting at different angles from substantially flat longitudinal faces defined on the external surface of the housing. If the longitudinal faces are not perfectly flat, however, the visual impairment may not be as noticeable. For example, if the device has a polygonal cross-section, and the faces of the polygon are very slightly outwardly curved, longitudinal faces of the device will have a slight transverse curvature. This slight curvature produces an optical effect that may disguise imperfect alignments between adjacent portions of the housing, which may not be as noticeable as if the faces were perfectly flat. While some curvature may be desirable, it is preferable that any convex curvature is not sufficient to facilitate rolling of the device. Thus, it is preferred that any curve delineating a face in the external cross-section of the device has a radius that is substantially greater than the distance across the face. In this way the device may be simultaneously aesthetically pleasing, have a pleasant ergonomic feel, and have an external shape that provides stability against rolling.

The outer housing of the aerosol-generating system may be manufactured from any suitable material or combination of materials. Examples of suitable materials include, but are not limited to, metallic materials and metals, alloys, polymers and plastics, or composite materials containing one or more of those materials, or thermoplastics that are suitable for food or pharmaceutical applications, for example polypropylene, polyetheretherketone (PEEK) and polyethylene. Preferred materials may include aluminium and aluminium alloys, acrylonitrile butadiene styrene (ABS), and polycarbonate (PC). When a metal, metallic material, or composite material comprising a metal is used, the surface may be anodized or otherwise treated to improve the appearance of and provide a scratch resistance surface for the device housing. Similarly, when the material does not comprise a metal, metallic material, or composite material, materials may be selected to optimize the appearance and functionality, e.g., scratch resistance, of the housing.

In a further aspect, there is also provided an aerosol-generating system. The system comprises an elongate aerosol-generating device as described above, and a charging device comprising a cavity having an opening suitable for receiving the aerosol-generating device.

Preferably, the aerosol-generating device comprises a means for keying the aerosol-generating device to the receiving cavity of the charging device. The keying means may comprise at least one notch for receiving at least one corresponding protrusion on the aerosol-generating device. The at least one protrusion may be a button adapted to activate the aerosol-generating device. Alternatively, the button of the device itself may function as the protrusion that facilitates keying. The aerosol-generating device receiving cavity may have a cross-sectional shape that corresponds to the cross-sectional shape of the aerosol-generating device. The keying means may then result from an enforced orientational relationship between the aerosol-generating device and the receiving cavity.

In one embodiment where the aerosol-generating device comprises at least one tapered end, the tapered end enables the device to be more easily inserted into the cavity of the charging device.

As used herein, means plus function features may be expressed alternatively in terms of their corresponding structure.

Any feature relating to one aspect may be applied to other aspects, in any appropriate combination. In particular, method aspects may be applied to apparatus aspects, and vice versa. Furthermore, any, some or all features in one aspect can be applied to any, some or all features in any other aspect, in any appropriate combination.

It should also be appreciated that particular combinations of the various features described and defined in any aspects of the invention can be implemented or supplied or used independently.

These and other aspects of the apparatus will become apparent from the following exemplary embodiments that are described with reference to the following figures in which.

Figure 1:
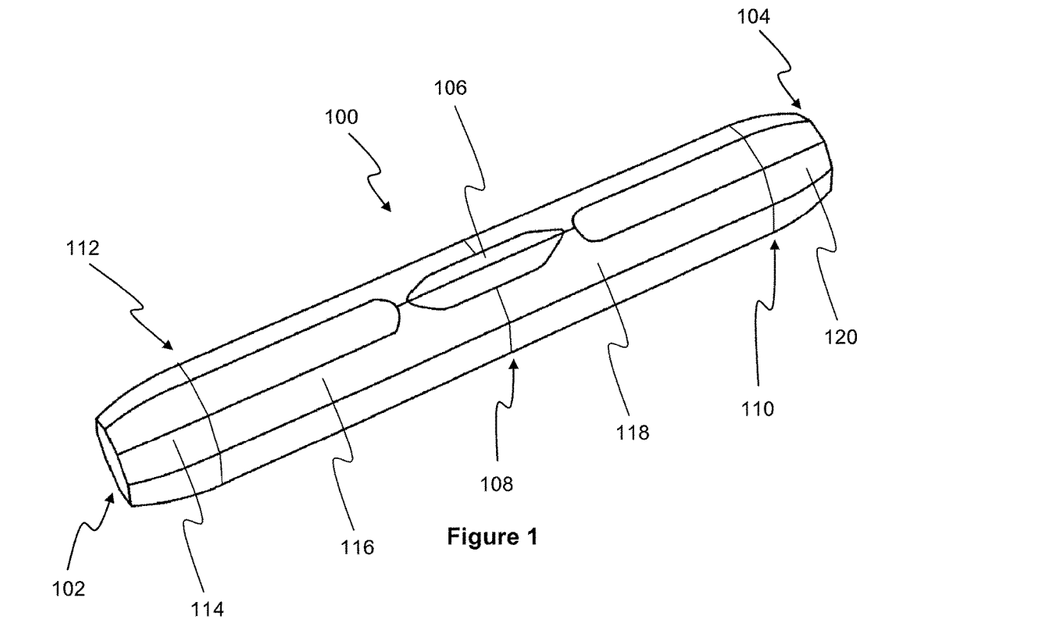
FIG. 1 shows a perspective view of one embodiment of an aerosol-generating device.

FIG. 1 shows a perspective view of one embodiment of an aerosol-generating device 100. The device 100 is elongate and comprises two opposed polygonal end faces 102 and 104 respectively. The device 100 also comprises a button 106 adapted to activate the aerosol-generating device when pressed. The operation of the device is described in further detail below. As can be seen, the outer housing of the device 100 comprises four portions joined at the coupling lines 108, 110 and 112 respectively. The outer housing is formed from an aluminium alloy having a wall thickness of approximately 0.3 mm. The four portions respectively are a first tapered end portion 114 attached to a first central portion 116, a second tapered end portion 120 attached to a second central portion 118. The four portions fit together around an inner housing (not shown) in a manner described below.

The device 100 has a regular polygonal cross-section along the majority of its length. However, in the region of the button 106 the cross-section is no longer a regular polygon, but remains a simple polygon.

Figure 2:
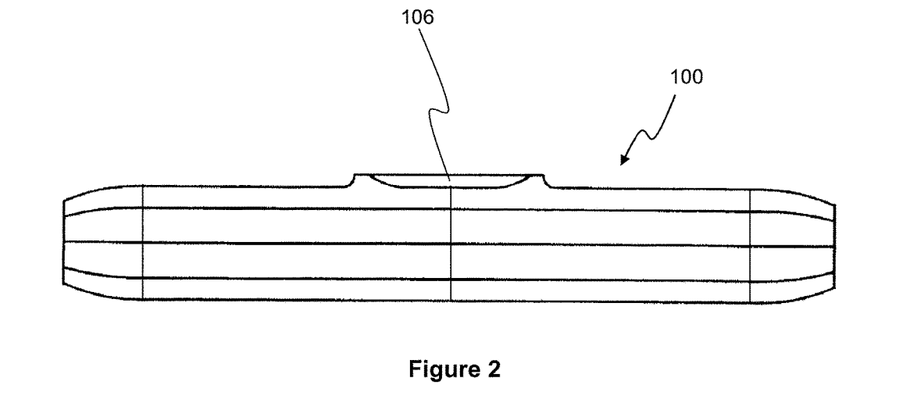
FIG. 2 shows a side-view of the aerosol-generating device shown in FIG. 1.

FIG. 2 shows a side-view of the aerosol-generating device 100 shown in FIG. 1. As can be seen, the button 106 protrudes from the surface of the device so that the user may more easily push the button to activate the device in use.

Figure 3A:
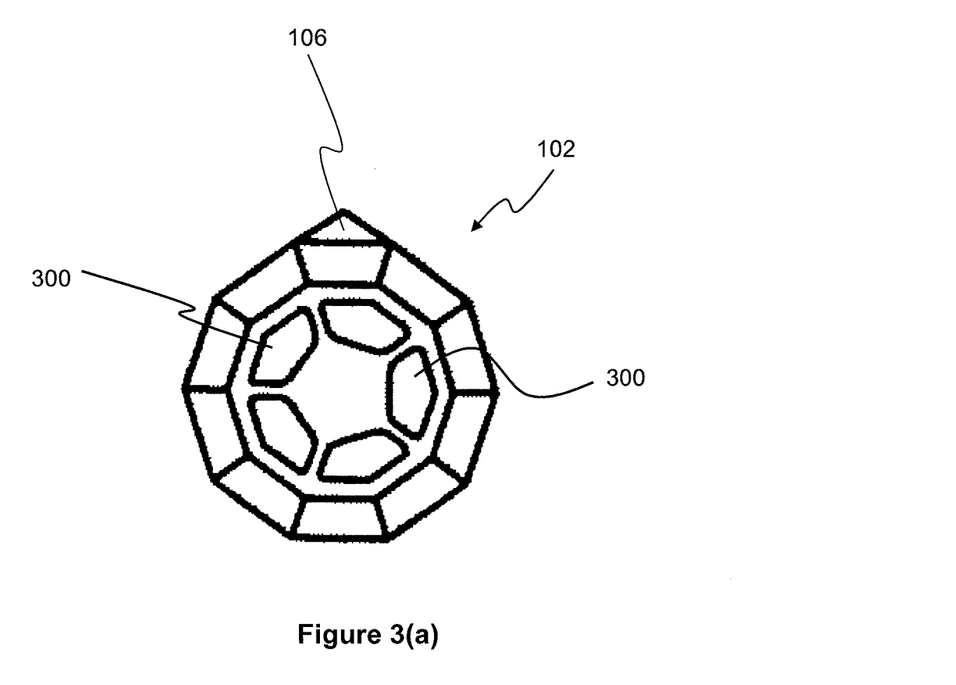
FIGS. 3(a) and 3(b) show end-views of the aerosol-generating device shown in FIGS. 1 and 2.
Figure 3B:
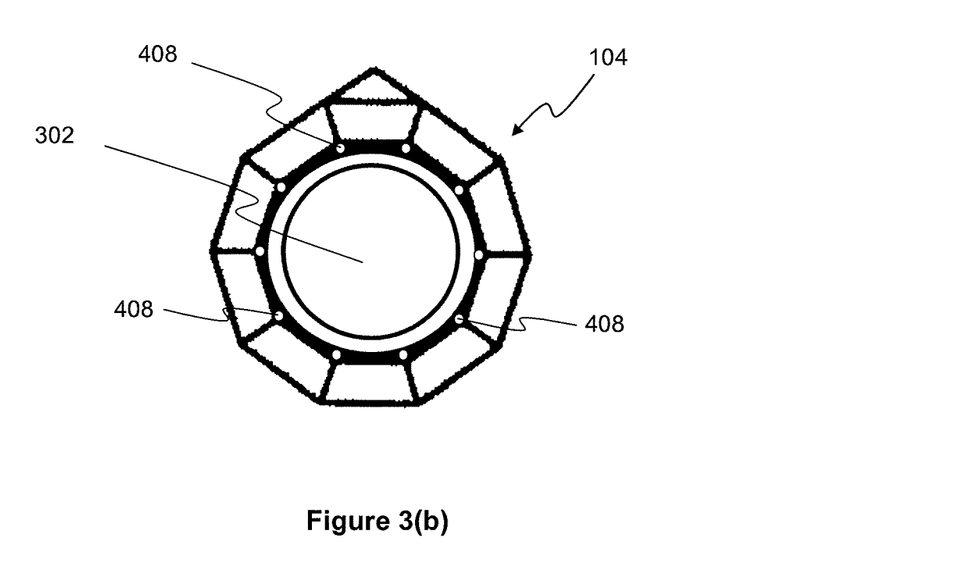

FIGS. 3(a) and 3(b) show the polygonal end faces 102 and 104 of the device 100 respectively. As can be seen, the polygon in this embodiment has ten sides, and this results in a device having ten longitudinally extending faces. The button 106 has a triangular cross-section and protrudes from one of the faces of the housing. This means that there is a flat face on the opposite side of the device to the button and the device may, therefore, be rested with the button 106 uppermost. It is noted that if the device were to have a cross-section defined by a polygon with an odd number of sides, it may be preferable for the button to be defined between faces such that it can be uppermost when the device is laying on a surface.

FIG. 3(a) shows the end face 102 of the coupling portion with five connectors or contacts 300. Connectors 300 may include one or more electrical connectors or one or more data connectors or a combination of electrical connectors and data connectors. The end face is part of an internal component of the device that is retained within the housing. The electrical connectors are adapted to connect with a secondary, charging, device which is described in further detail below. As can be seen, providing a polygonal cross-section allows for the five electrical connectors 300 to more easily be positioned on the end face 102 of the aerosol-generating device 100.

FIG. 3(b) shows the end face 104. A holder 402 defining a cavity 302 is provided to accept an aerosol-generating article comprising an aerosol-forming substrate (not shown).

Figure 4A:
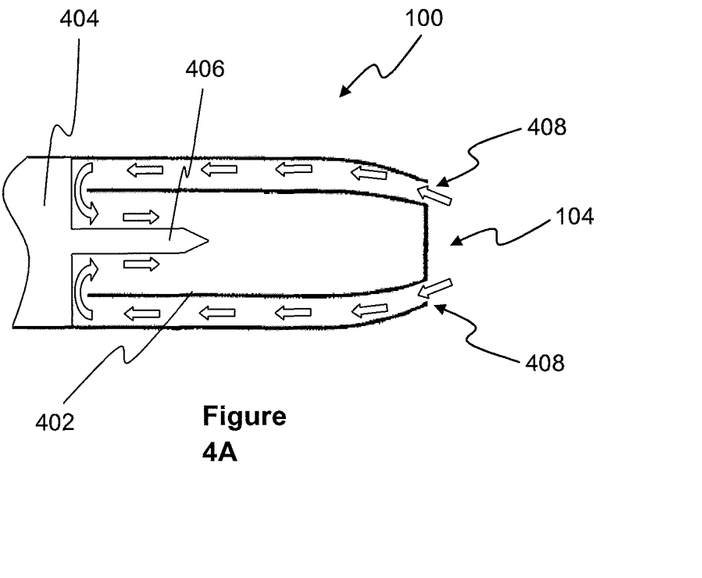
FIGS. 4(a) and 4(b) illustrate a schematic diagram of the air flow through the aerosol-generating device shown in FIGS. 1, 2 and 3.
Figure 4B:
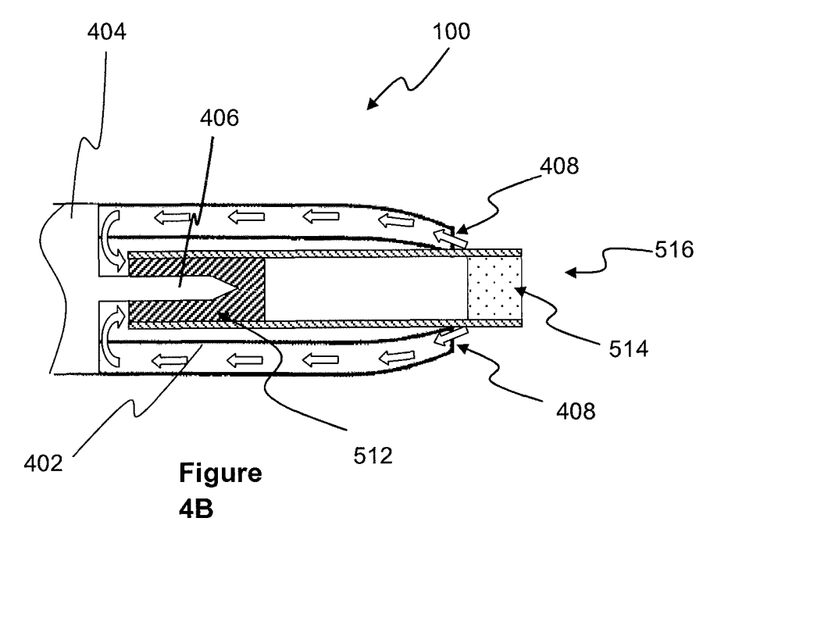

FIGS. 4A and 4B show a schematic representation of the air flow through the device. It is noted that these figures do not accurately depict the relative scale of elements of the device, for example the inlet channels. As can be seen in this embodiment, when an aerosol-generating article 304 is received within the cavity 302 of the device 100 (FIG. 4B), air drawn into the device passes around the outside of a aerosol-generating article holder 402 located within cavity 302. The holder 402 has a circular cross-section. The drawn air proceeds into the aerosol-forming substrate at the distal end of the smoking article adjacent a heating bushing 404 of a blade shaped heating element 406 provided in the cavity 302. The drawn air proceeds through the substrate, entraining the aerosol, and then to the mouth end of the smoking article. Air inlets 408 formed between the outer housing and the holder 402 enable air to be entrained more efficiently and aid with insulating the heated aerosol-generating article from the outer housing. The air inlets 408 may be seen schematically in FIG. 3(b). It is noted that the inlets may not be circular, but they are depicted as circular in FIG. 3(b) for clarity.

Figure 5:
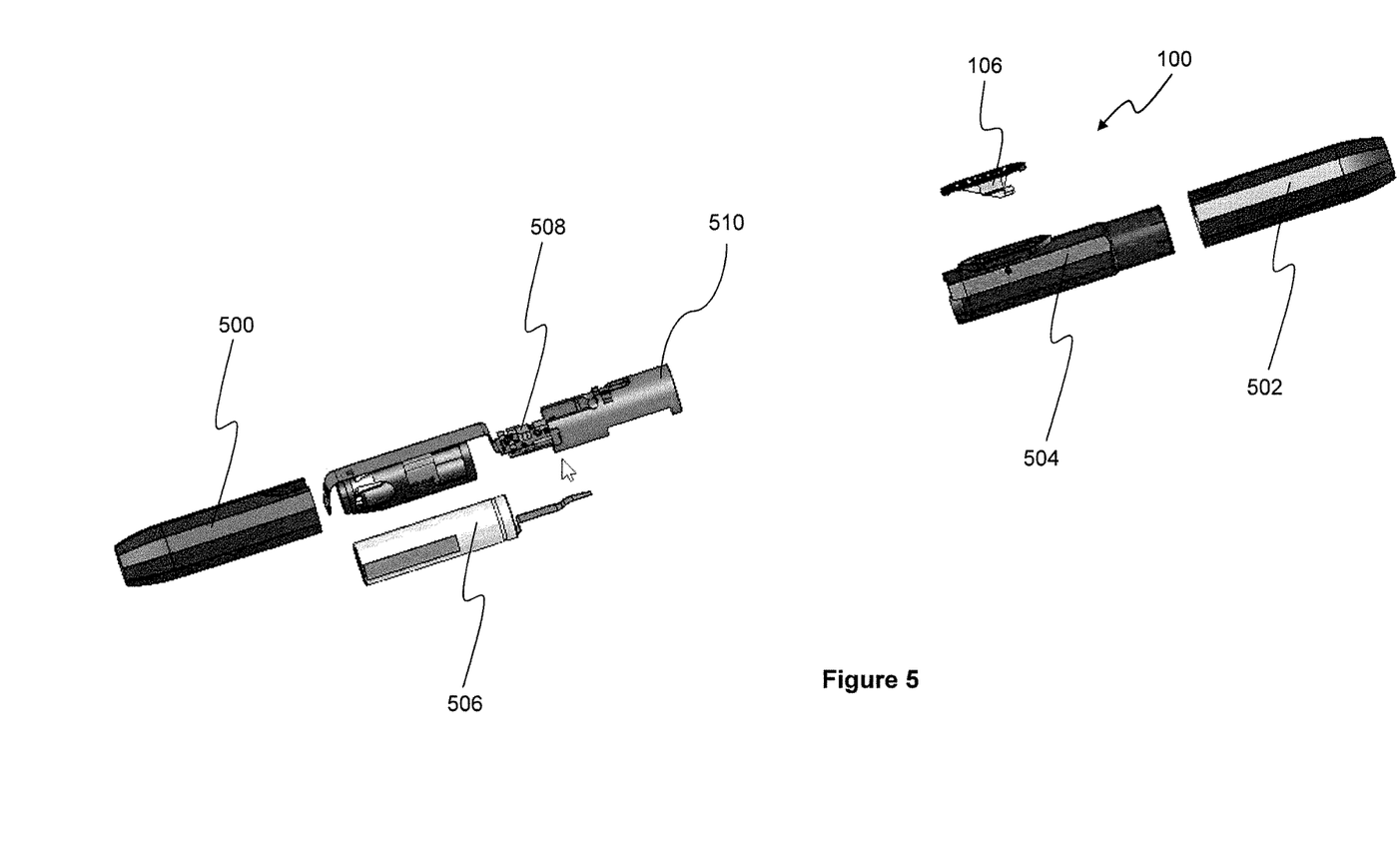
FIG. 5 shows an exploded view of the aerosol-generating device shown in FIGS. 1, 2 and 3.

FIG. 5 shows an exploded view of the aerosol-generating device 100. The device comprises a first outer housing portion 500 comprising the first tapered end portion 114 and the first central portion 116. The device further comprises a second outer housing portion 502 comprising the second tapered end portion 120 and the second central portion 118. The device also comprises an inner housing 504. The device also comprises a power supply in the form of a battery 506, a controller 508 adapted to control the power supplied from the battery 506 to a heating element (not shown) contained in an internal housing section 510. The button 106 is located in the central housing portion 504, and engages with the controller 508 to enable the user to activate the device.

In use, a user inserts an aerosol-generating article 516 comprising an aerosol-forming substrate 512 into the cavity 302 of the aerosol-generating device 100. The aerosol-forming substrate 512 engages with the heating element 406. When the user activates the device by pushing button 106, power is supplied to the heating element 406 from the battery 506 via the controller 508. The heating element 406 heats the aerosol-forming substrate 512 to generate an aerosol and the aerosol is entrained within the air flow as the user draws on the mouth end 514 of the aerosol-generating article 516.

Figure 6A:
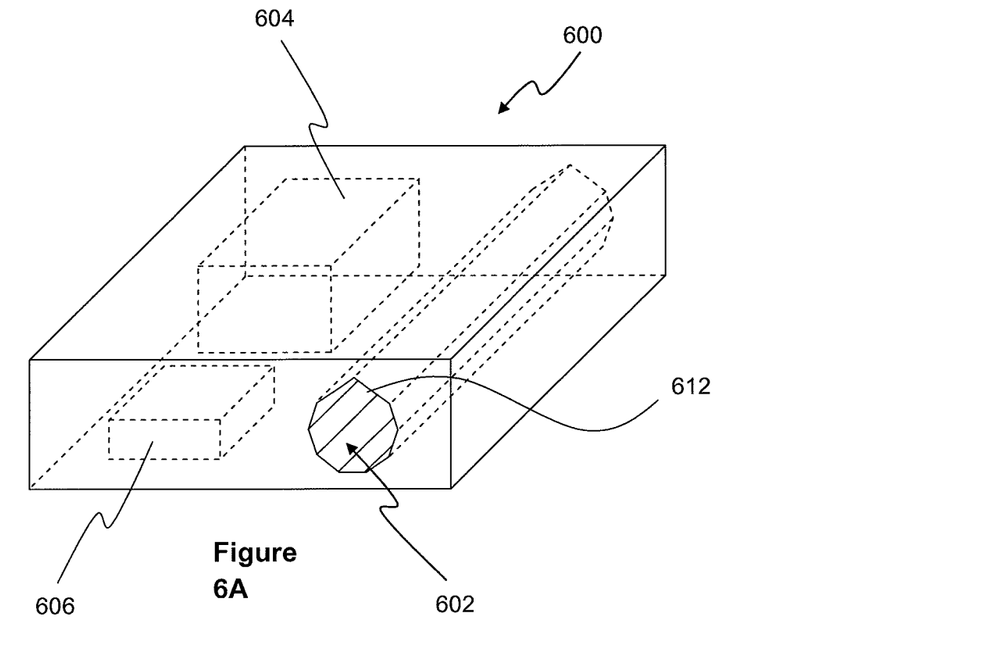
FIGS. 6(a) and 6(b) illustrate a charging device adapted to receive and charge the aerosol-generating device shown in FIGS. 1 to 5.
Figure 6B:
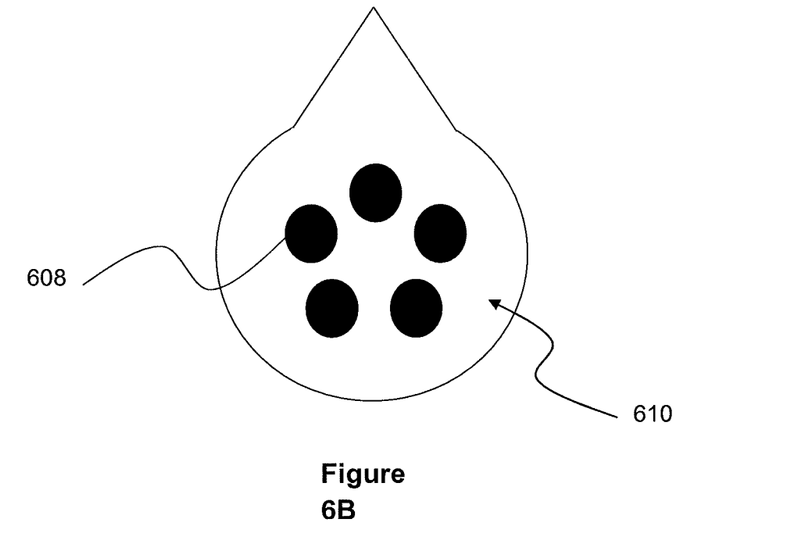

FIG. 6A shows a perspective view of a charging device 600 adapted to receive and charge the aerosol-generating device 100. The charging device comprises a cavity 602 adapted to receive the aerosol-generating device 100, a power supply in the form of a battery 604, and a controller 606. When the device 100 requires charging or data is to be communicated between the devices 100 and 600, device 100 is inserted into the cavity 602, and the connections 300 are coupled to corresponding contacts 608 of contact plate 610 at the bottom of the cavity 602. FIG. 6B is a schematic diagram illustrating the contact plate 610 of the charging device, which is located at the bottom of the cavity 602. The contact plate can be seen to have five contacts 608, which correspond to the five contacts 300 on the aerosol-generating device.

The cavity 602 has a polygonal cross-section that corresponds to the cross-section of the aerosol-generating device 100. The cavity could, alternatively, have a substantially circular cross-section of diameter sufficient to receive the device. In addition, the cavity is provided with a notch 612 that allows the button 106 of the device to be located within the cavity 602. Button 106 on the device 100 allows the device to be keyed to the charging device 600 such that the device 100 may only be inserted into the charging device 600 in one orientation. By providing such a keying means, the user is prevented from inserting the device 100 incorrectly, and thus the correct connections 300 of device 100 and contacts 610 are made every time the device 100 is inserted in device 600. In addition, the tapered end portion 114 of the aerosol-generating device 100 allows the user to more easily insert the device into the cavity 602.

Figure 7:
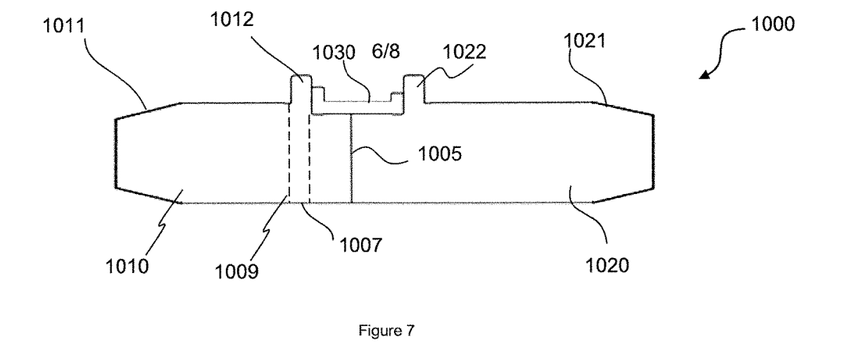
FIG. 7 shows a schematic side view of a second embodiment of an aerosol-generating device.

FIG. 7 shows a projection of an embodiment of an aerosol-generating device 1000. The device comprises a first housing portion 1010 and a second housing portion 1020. Both housing portions are substantially elongate tubes having a decagonal transverse cross-section. When assembled, the first housing portion and the second housing portion meet at a join 1005. Join 1005 may alternatively be placed at other locations, such as locations indicated by lines 1007 or 1009, illustrated in FIG. 7. By providing join 1005 at locations 1007 or 1009, additional flexibility regarding the size of first and second housing portions 1010 and 1020 are provided.

A button 1030 extends through the housing. The button 1030 is connected to internal electronics and allows a user to actuate the device. Projections 1012, 1022 extend from each housing portion adjacent to the button. These projections accentuate the position of the button 1030, thereby allowing a user to actuate the device without looking to see the position of the button. These projections 1012, 1022 also serve a keying function when the device 1000 is coupled to a secondary unit. These projections 1012, 1022 also help shield the button and prevent accidental actuation of the device. These projections 1012, 1022 also contribute to the stability of the device by acting as barriers to the rolling of the device. As will now be apparent to one of ordinary skill in the art, the inclusion of projections 1012 and 1022 is optional as button 106 may provide equivalent functionality, as discussed in connection with FIGS. 1, 2, 3(a), and 3(b) above.

A terminal end of the first housing portion 1010 is tapered 1011. A terminal end of the second housing portion 1020 is tapered 1021. The housing portions are formed from injection moulded polycarbonate (PC) having a wall thickness of approximately 0.75 mm. The injection mouldings were produced with injection points at an end of the mould and flow lines of the injected polymer extending along the longitudinal axis of each housing portion. The total length of the device is approximately 94 mm.

The outer cross-section of each housing portion is decagonal. The faces of the decagon 1100 are slightly curved so that the cross-section is a convex decagon. This is illustrated schematically in FIG. 8 where the dotted lines represent a perfect decagon, and the solid lines represent a convex decagon. It is noted that the curvature shown in FIG. 8 has been exaggerated considerably for illustrative purposes.

Figure 8:
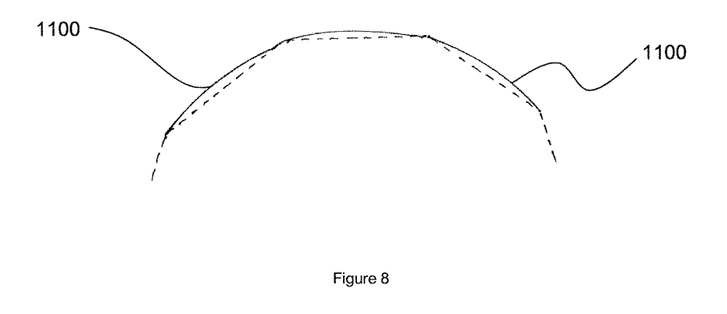
FIG. 8 illustrates the convex decagonal external transverse cross-section of the device of FIG. 7.

When the device 1000 is assembled and the first housing portion 1010 abuts the second housing portion 1020 at the join 1005, the slightly curved decagonal faces 1100 produce an optical effect that does not accentuate any mismatch or misalignment in the two housing portions.

The first housing portion 1010 defines a substrate receiving cavity as described above in relation to the embodiment of FIG. 1. This housing portion 1010 may be slideably separated from the second housing portion 1020 by sliding in a longitudinal direction. The first housing portion 1010 may be removed from the device 1000 entirely.

Figure 9:
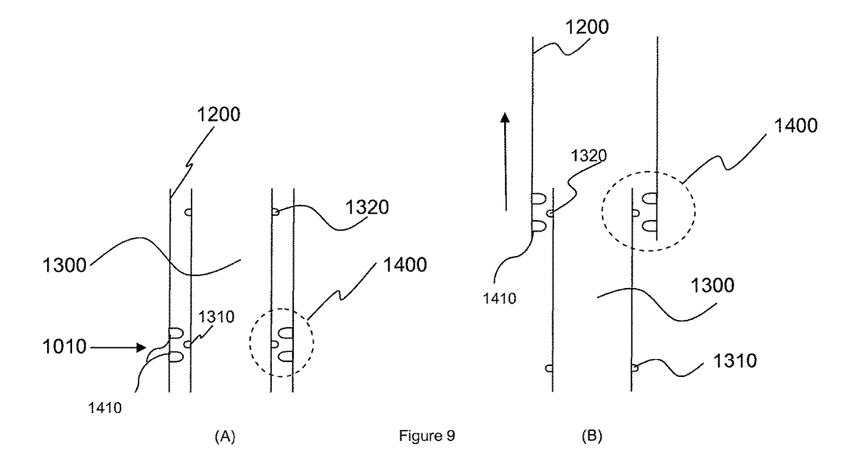
FIGS. 9A and 9B are schematic diagrams illustrating the use of snaps defined on an internal surface of a housing portion to retain the housing portion on the device.
Figure 10:
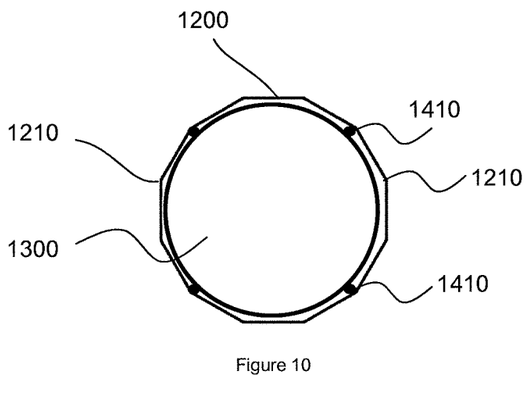
FIG. 10 is a schematic cross-sectional illustration of an inner surface of a housing portion showing the circumferential location of snaps of FIG. 9.

An inner surface 1200 of the first housing portion 1010 may have a decagonal cross-section or alternatively may be substantially cylindrical in shape. This inner surface 1200 engages with an internal body portion 1300 of the device that is substantially cylindrically shaped. The first housing portion 1010 is retained on the device 1000 by means of snaps 1400 (see regions outlined by circles in FIG. 9). The snaps 1400 comprise a combination of protrusions 1410 located on an inner surface of the housing portion with sprung protrusions 1310 or 1320 located on an outer surface of an inner body. The inner surface 1200 of the first housing portion 1010 has four pairs of longitudinally spaced protrusions 1410 that are circumferentially spaced within the inner surface 1200. These pairs of protrusions 1410 engage with sprung protrusions 1310, 1320 projecting from the inner body 1300. When the first portion of the housing 1010 abuts the second portion 1020, the pairs of protrusions 1410 engage with a first set of sprung protrusions 1310. The first housing portion 1010 is thereby retained against the second housing portion 1020.

By applying a force in a longitudinal direction, snaps 1400 are disengaged when the protrusions 1410 on the first housing portion 1010 disengage with the first set of sprung protrusions 1310 and the first housing portion 1010 may freely slide in a longitudinal axis. To retain the first housing portion 1010 in a second position, longitudinally spaced from the first position, the protrusions 1410 may engage with a second sprung protrusions 1320 located on the inner body 1300 and snaps 1400 are reengaged with the combination of protrusions 1410 and 1320. The second sprung protrusions 1320 are longitudinally spaced from the first sprung protrusions 1310. The sprung protrusions 1310, 1320 may be sprung by cantilever springs.

Figure 11:
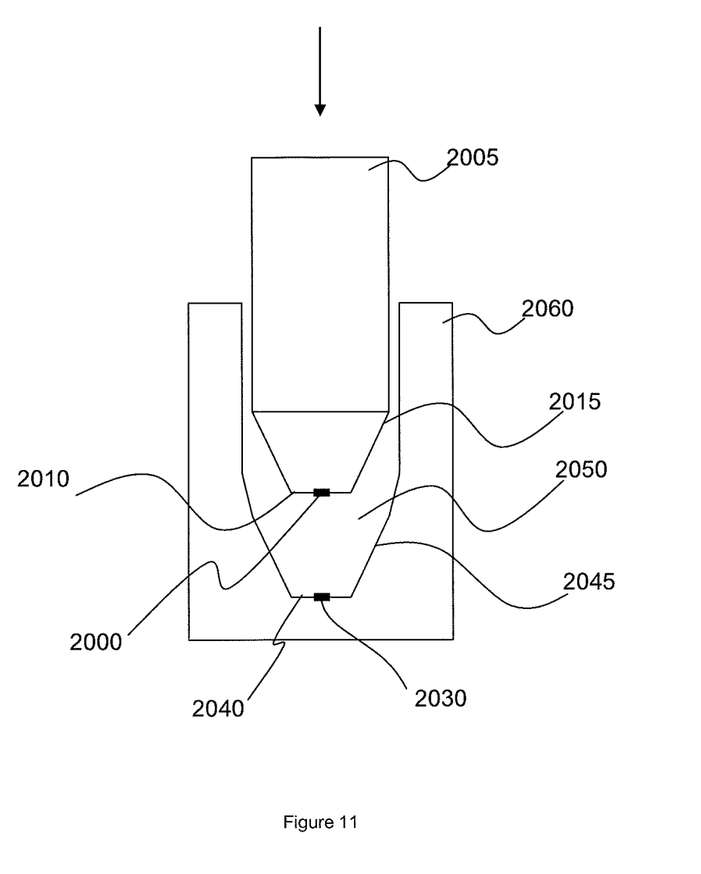
FIG. 11 is a schematic illustration showing a tapered aerosol-generating device being inserted into a cavity of a charging device to make an electrical connection between contacts located on the aerosol-generating device and the charging device respectively.

As discussed above, it may be advantageous for an aerosol-generating device to comprise at least one tapered end. FIG. 11 is a schematic illustration of one end of an aerosol-generating device 2005 having an exemplary connection 2000 located at an end-face 2010. The connection 2000 on the aerosol-generating device 2005 is couplable to a contact 2030 located at a terminal face 2040 of a device receiving cavity 2050 of a charging device 2060. An internal wall 2045 of the device receiving cavity 2050 is tapered to approximate the tapered surface 2015 of the aerosol-generating device 2005. As the aerosol-generating device is inserted into the cavity 2050, the tapered surfaces 2015, 2045 impinge and guide connection 2000 and contact 2030 into alignment. It will now be apparent to one of ordinary skill in the art that the connection 2000 and contact 2030 may comprise one of connections 300 and one of contacts 608 discussed in relation to FIG. 3(b) above and that such connections and contacts may facilitate transfer of electrical charge or data between the aerosol-generating device and charging device discussed herein.

Other details of the construction and use of this embodiment are the same as described above in relation to the embodiment of FIG. 1.

It is of course to be understood that the specification is not intended to be restricted to the details of the above embodiments which are described by way of example only.

The invention claimed is:

1. An aerosol-generating system, comprising:
    an elongate aerosol-generating device in which at least a portion of the device has a transverse external cross-section defined by a shape having at least five sides, wherein the external cross-section is a shape defining an outer circumcircle having a diameter of between 10 mm and 20 mm, the shape having at least five corners joined by curves; and
    a charging device comprising a cavity having a polygonal transverse cross-section corresponding to the transverse external cross-section of the elongate aerosol-generating device, the cavity being configured to receive the elongate aerosol-generating device,
    wherein the cavity comprises at least one notch for receiving configured to receive at least one corresponding protrusion on the elongate aerosol-generating device, and
    wherein the at least one protrusion is a button configured to activate the elongate aerosol-generating device.

2. The elongate aerosol-generating system according to claim 1, wherein the elongate aerosol-generating device is substantially cylindrical.

3. The elongate aerosol-generating system according to claim 1, wherein the elongate aerosol-generating device is between 60 mm and 150 mm in length, and the cross-sectional shape comprises between seven and twelve sides, each side being greater than 2 mm long.

4. The elongate aerosol-generating system according to claim 1, wherein the external cross-sectional shape is a polygon.

5. The elongate aerosol-generating system according to claim 1, wherein at least one end of the elongate aerosol-generating device is tapered.

6. The elongate aerosol-generating system according to claim 1, wherein an external shape of the elongate aerosol-generating device is defined by a housing, the housing comprising an elongate shell having a length of between 60 mm and 150 mm and a wall thickness of between 0.2 mm and 1 mm.

7. The elongate aerosol-generating system according to claim 6, wherein the housing comprises first and second elongated portions, the first and second elongated portions being separable from one another.

8. The elongate aerosol-generating system according to claim 6, wherein the housing is formed from a polymer having a wall thickness of between 0.5 mm and 1 mm.

9. The elongate aerosol-generating system according to claim 6, wherein the housing has an internal cross-section, at least a portion of the internal cross-section being non-circular.

10. The elongate aerosol-generating system according to claim 1, further comprising:
   a substrate receiving cavity configured to receive an aerosol-forming substrate;
   a heating element configured to heat an aerosol-forming substrate to generate an aerosol; and
   a power supply configured to provide power to the heating element.

* * * * *